United States Patent
Lanz et al.

(10) Patent No.: US 9,320,453 B2
(45) Date of Patent: Apr. 26, 2016

(54) ASSEMBLY TO PERFORM IMAGING ON RODENTS

(75) Inventors: Titus Lanz, Rimpar (DE); Michael Sauer, Rimpar (DE); Frank Resmer, Rimpar (DE)

(73) Assignee: RAPID BIOMEDICAL GMBH, Rimpar (DE)

( * ) Notice: Subject to any disclaimer, the term of this patent is extended or adjusted under 35 U.S.C. 154(b) by 817 days.

(21) Appl. No.: 13/590,842

(22) Filed: Aug. 21, 2012

(65) Prior Publication Data

US 2012/0330130 A1  Dec. 27, 2012

Related U.S. Application Data (63) Continuation-in-part of application No. 13/464,063, filed on May 4, 2012, now abandoned.

(60) Provisional application No. 61/483,256, filed on May 6, 2011, provisional application No. 61/483,281, filed on May 6, 2011.

(51) Int. Cl.
| | |
|---|---|
| *A61B 5/055* | (2006.01) |
| *A61B 6/04* | (2006.01) |
| *A61D 7/04* | (2006.01) |
| *A01K 1/06* | (2006.01) |
| *A61B 6/00* | (2006.01) |

(52) U.S. Cl.
CPC .............. *A61B 5/0555* (2013.01); *A01K 1/0613* (2013.01); *A61B 6/0407* (2013.01); *A61B 6/0421* (2013.01); *A61B 6/4417* (2013.01); *A61B 6/508* (2013.01); *A61D 7/04* (2013.01)

(58) Field of Classification Search
CPC ...... A61B 6/04; A61B 6/0407; A61B 6/0421; A61B 6/508; A61B 5/055; A61B 5/0555; A61D 7/04; A01K 1/0613
USPC .............. 5/601, 600, 621, 622; 378/209, 208; 119/417, 420, 755, 756; 600/407, 415, 600/421, 422
See application file for complete search history.

(56) References Cited

U.S. PATENT DOCUMENTS

| | | |
|---|---|---|
| 4,721,060 A | 1/1988 | Cannon et al. |
| 4,860,741 A | 8/1989 | Bernstein et al. |
| 5,099,792 A | 3/1992 | Cannon et al. |
| 5,297,502 A | 3/1994 | Jaeger |
| 5,601,570 A * | 2/1997 | Altmann et al. ............... 606/130 |
| 5,896,829 A | 4/1999 | Rothenberg et al. |
| 6,258,103 B1 * | 7/2001 | Saracione ..................... 606/130 |
| 6,275,723 B1 | 8/2001 | Ferris et al. |
| 6,651,587 B1 | 11/2003 | DeFord et al. |
| 6,711,430 B1 | 3/2004 | Ferris et al. |
| 6,716,220 B2 * | 4/2004 | Saracione ..................... 606/130 |

(Continued)

FOREIGN PATENT DOCUMENTS

| | | |
|---|---|---|
| CA | 2426324 C | 4/2002 |
| DE | 10015670 A1 | 10/2001 |

(Continued)

*Primary Examiner* — Robert G Santos
(74) *Attorney, Agent, or Firm* — Pearne & Gordon LLP (57) ABSTRACT

An imaging device for imaging an anaesthetized animal such as a rodent (rats or mice or other animals), with the device having a split array coil capable of providing at least two channels for use in a restraining assembly with animal bed for magnetic resonance imaging (MRI) the animal in real-time in a non-destructive manner.

22 Claims, 7 Drawing Sheets

(56) References Cited

U.S. PATENT DOCUMENTS

| | | |
|---|---|---|
| 6,776,158 B1 | 8/2004 | Anderson et al. |
| 6,873,156 B2 | 3/2005 | Ferris et al. |
| 6,904,912 B2 | 6/2005 | Roy et al. |
| 7,343,194 B2 | 3/2008 | Ferris et al. |
| 7,377,276 B2 | 5/2008 | Roy et al. |
| 7,414,403 B2* | 8/2008 | Chiodo ............... 324/321 |
| 7,534,067 B2* | 5/2009 | Chiodo ............... 403/350 |
| 7,784,429 B2* | 8/2010 | Chiodo ............... 119/417 |
| 7,865,226 B2* | 1/2011 | Chiodo ............... 600/407 |
| 8,322,310 B2* | 12/2012 | Chiodo ............... 119/755 |
| 8,334,698 B2* | 12/2012 | Tammer et al. ....... 324/321 |
| 8,342,136 B2* | 1/2013 | Hadjioannou et al. .. 119/755 |
| 8,482,278 B2* | 7/2013 | Wolke et al. ........ 324/307 |
| 8,578,889 B2* | 11/2013 | Chiodo ............... 119/420 |
| 8,774,899 B2* | 7/2014 | Chiodo ............... 600/415 |
| 8,851,018 B2* | 10/2014 | Rapoport et al. ..... 119/420 |
| 2001/0053878 A1 | 12/2001 | Ferris et al. |
| 2003/0125753 A1* | 7/2003 | Saracione ............ 606/130 |
| 2004/0204642 A1 | 10/2004 | Ferris et al. |
| 2004/0216737 A1 | 11/2004 | Anderson et al. |
| 2005/0027190 A1* | 2/2005 | Chiodo ............... 600/415 |
| 2007/0169717 A1 | 7/2007 | Conger et al. |
| 2007/0175404 A1 | 8/2007 | Conger et al. |
| 2007/0238946 A1* | 10/2007 | Chiodo ............... 600/407 |
| 2007/0244422 A1 | 10/2007 | Chiodo |
| 2008/0047554 A1 | 2/2008 | Roy et al. |
| 2008/0072836 A1* | 3/2008 | Chiodo ............... 119/417 |
| 2008/0168951 A1 | 7/2008 | Starr et al. |
| 2009/0000567 A1* | 1/2009 | Hadjioannou et al. .. 119/755 |
| 2009/0245474 A1* | 10/2009 | Chiodo ............... 378/208 |
| 2010/0056899 A1* | 3/2010 | Toddes et al. ........ 600/411 |
| 2010/0072999 A1* | 3/2010 | Wolke et al. ........ 324/309 |
| 2010/0188087 A1* | 7/2010 | Tammer et al. ....... 324/321 |
| 2010/0269260 A1* | 10/2010 | Lanz et al. ........... 5/601 |
| 2011/0092807 A1* | 4/2011 | Chiodo ............... 600/421 |
| 2012/0073509 A1* | 3/2012 | Rapoport et al. ..... 119/420 |
| 2012/0278990 A1* | 11/2012 | Lanz et al. ........... 5/601 |
| 2012/0330130 A1* | 12/2012 | Lanz et al. .......... 600/411 |
| 2013/0061812 A1* | 3/2013 | Chiodo ............... 119/420 |

FOREIGN PATENT DOCUMENTS

| | | |
|---|---|---|
| FR | 2007135248 A1 | 11/2007 |
| WO | WO023206 A2 | 4/2002 |

* cited by examiner

ASSEMBLY TO PERFORM IMAGING ON RODENTS

CROSS-REFERENCES TO RELATED APPLICATIONS

This application is a continuation-in-part of U.S. patent application Ser. No. 13/464,063, filed on May 4, 2012, incorporated herein by reference, which claims the benefit of U.S. provisional application Ser. No. 61/483,256 filed on May 6, 2011, incorporated herein by reference, and also claims the benefit of U.S. provisional application Ser. No. 61/483,281 filed on May 6, 2011, and also incorporated herein by reference.

BACKGROUND OF THE INVENTION

This application relates generally to an animal holding device for holding an animal during an imaging operation.

More specifically, this application relates to an apparatus and method including a restraining assembly for an anaesthetized rodent (rats or mice or other) in combination with a split array coil for magnetic resonance imaging (MRI) the animal in real-time in a non-destructive manner.

Rodents and other laboratory animals are often used for testing purposes. Such testing may involve the need to scan the animal using a scanning device, such as an SPECT, PET, CT, CAT, X-Ray, NMR/MR, or other imaging device, to provide real time and/or photographic images of the animal, which may be done in a non-destructive manner. It is often desirable to anesthetize such animals in order to completely immobilize the animal during the scanning process. Anesthetized animals, and in particular rodents, often cannot hold their body temperature at desired temperatures during such procedures, potentially leading to stress on the animal.

A system and method of maintaining the body temperature of immobilized animals in a consistent state while the animal is being anesthetized and/or while the animal is being scanned, or otherwise utilized by the testing process was disclosed in U.S. patent application Ser. No. 12/430,487, filed on Apr. 27, 2009, and incorporated herein by reference. Jürgen E. Schneider et al.: "Ultra-Fast and Accurate Assessment of Cardiac Function in Rats Using Accelerated MRI at 9.4 Tesla. Magnetic Resonance in Medicine" 59: 636-641 (2008), also incorporated herein by reference, discusses such concepts.

With live animals, it is always desirable to keep the time of the experiment as short as possible so that the stress on the animal is kept to a minimum. An assembly where the skull is fixed at the position of the animal's ears with two pins that form a stereotactic holder provides a stereotactic fixation such that the position of the animal's skull is well defined. The usual neurological set-up of a life animal incorporates a minimum of 3 positioning points. This is the bar to fixate the animal's teeth, and two pins for the locking of the skull via the animal's ears (left and right). However, it is often difficult to find the correct pressure to securely fixate the animal and lock it securely in one position and not harm the animal (e.g. perforate its ear drums). Due to the set-up from both sides of the animal's head, it is relatively time consuming to lock the animal head and to position it in the centre of the assembly, and so poses additional stress to the animal. The stereotactic set-up with ear pins also consumes valuable space and so limits the coil's filling factor.

A head coil assembly used in MRI imaging can be either carried out as a cylindrical volume coil enveloping the animal, or as a surface coil or surface array positioned directly on top of the animal head. This MR volume coil has clear advantages when good homogeneity is desired, as the image intensity is distributed relatively even over the volume. A good homogeneity is very important for qualitative measurements and QA set-ups. However, a small positioning error can lead to large changes in the signal intensity, and affect the measurement. However the volume coil has a low sensitivity and the image SNR at the position of the animal brain is usually much lower than with a local surface coil positioned above the animal skull. Although the surface coil has clear SNR advantages over the volume coil, its signal sensitivity drops rapidly when moving away from the coil. So both, the penetration depth and the homogeneity of the surface coil are rather poor.

MR investigations of the animal's heart use a different set-up in comparison to neurological investigations of the animal brain. An assembly composed of one or more MR loops is housed inside a thin semi cylinder or a flat structure when imaging the heart. Here, the animal is usually positioned on top of the coil to reduce motion artefacts and also to minimize the distance of the coil to the animal's heart.

Desirable is a device for supporting the anesthetizing and scanning process that is compatible with desired scanning functions, such that the animal can be imaged in an optimum position and with a coil size that can be adjusted to the particular size of the animal's head for maximum filling factor and optimum signal-to-noise-ratio (SNR). Also desirable is positioning that can be reproduced in later experiments. It would also be useful to reduce or eliminate as much animal movement as possible to supress motion artifacts during an MR experiment, and to reduce setup times to minimize the stress of the animals.

SUMMARY OF THE INVENTION

Provided is a restraining assembly for an anaesthetized rodent (rats or mice or other) in combination with a split array coil for magnetic resonance imaging (MRI). In one example embodiment, the restraining assembly is designed for imaging the complete head, or alternatively the complete heart, of the animal. The assembly allows adjustment so that the animal can be imaged in an optimum position and so that the coil size can be adjusted to the particular size of the animal's head for maximum filling factor and optimum signal-to-noise-ratio (SNR). The positioning can be reproduced in later experiments. The assembly further includes parts that largely eliminate remaining animal movement and so supress motion artefacts during an MR experiment.

The MR coil of an example embodiment includes two parts—a bottom part and a top part. The bottom part supports the animal skull (or the torso) and receives the MR signal from the lower part of the animal, whereas the coil's top part receives the MR signal from the upper part of the head or torso. A preamplifier may be provided for each part, in some cases integrated in the parts themselves. In this example embodiment, both coil parts are integral parts of the restraining assembly; however these coil parts can also be removed from the set up. It is also possible to use only one of the two parts of the array without the other part. Each of the parts can provide an imaging channel. With the standard work flow the bottom part is usually kept assembled in the restraining assembly whereas the top part can be removed to allow a correct positioning of the animal. A pivot allows the final adjustment of the bottom part of the head coil so that the animal head is positioned directly against the top part for maximum filling factor and optimum signal to noise ratio (SNR).

Thus provided is an embodiment of an apparatus for supporting the imaging of an animal, comprising: an animal bed; a first part positioned with the bed for supporting a part of the animal and receiving a first imaging signal from a first portion of the animal; and a second part connected to the bed for receiving a second imaging signal from a second portion of the animal, wherein the first part and the second part are separately moveable with respect to the animal bed.

Further provided is another embodiment of an apparatus for supporting the imaging of an animal, comprising: an animal bed; a bottom array part connected to the bed and including a first coil adapted for receiving a first imaging signal from a lower part of the animal; a top array part including: a second coil adapted for receiving a second imaging signal from the head and/or torso of the animal, an inner portion that is anatomically formed to accommodate the head and/or torso of the animal, and a removable connection connected to the bed for allowing the top part to be removed from the bed; and an adjustment mechanism for adjusting a height of the first part of the array coil to accommodate the size of the head of the animal.

Also provided is an embodiment of apparatus for supporting the imaging of an animal, comprising: an animal bed; a bottom array part connected to the bed and including a first coil adapted for receiving a first imaging signal from a lower part of the animal, a top array part including: a second coil adapted for receiving a second imaging signal from the head and/or torso of the animal, and a removable connection connected to the bed for allowing the top part to be removed from the bed and also for allowing the top part to be pivoted away from the second part; an adjustment mechanism for adjusting a height of the first part of the array coil to accommodate the size of the head of the animal in a repeatable manner; an anesthetic unit connected to the bed and provided within the bottom array part and the top array part, wherein when the top array part is pivoted away from the bottom array part, access is provided to the anesthetic unit; and a head holding mechanism connected to the bed for holding the head of the animal in a fixed position.

Further provided is an apparatus for supporting the imaging of an animal, comprising: an animal bed; a bottom array part including: a bottom part connection mechanism for connecting to the bed in a pivoting manner; a bottom part locking mechanism for locking the bottom part in place for imaging the animal, and a first coil adapted for receiving a first imaging signal from a lower part of the animal; a top array part including: a top part connection mechanism for connecting to the bed in a pivoting and removable manner, a top part locking mechanism for locking the top part in place for imaging the animal, a second coil adapted for receiving a second imaging signal from the head and/or torso of the animal, and an inner portion that is anatomically formed to accommodate the head and/or torso of the animal; an adjustment mechanism for adjusting a height of the first part of the array coil to accommodate the size of the animal in a repeatable manner; a friction place interacting with the adjustment mechanism to prevent inadvertent misadjustment; an adjustment locking mechanism for locking the adjustment mechanism in place for imaging the animal; a removable anesthetic unit connected to the bed and provided within the bottom array part and the top array part, wherein when the top array part is pivoted away from the bottom array part, access is provided to the anesthetic unit, wherein access to the anesthetic unit and/or the animal is provided by pivoting the top part and the bottom part away from each other.

Also provided are additional example embodiments, some, but not all of which, are described hereinbelow in more detail.

BRIEF DESCRIPTION OF THE DRAWINGS

The features and advantages of the example embodiments described herein will become apparent to those skilled in the art to which this disclosure relates upon reading the following description, with reference to the accompanying drawings, in which.

DETAILED DESCRIPTION OF THE EXAMPLE EMBODIMENTS

FIGS. 1-7 provide a first example embodiment of an imaging assembly for imaging a mouse, with the assembly comprising a combined array coil including a top part 1 and a bottom part 2. The coil parts contain the electrical coils for performing the imagings. The two coil parts 1, 2 can be separated from the coil holder 17 (see FIGS. 3 & 17) to allow for a correct sample positioning. Each of the coil parts 1, 2 can operate as a separate channel for the imaging signal(s). The assembly parts can be adjusted to the size of the sample, so that the animal head is fixed in position (e.g., using the gas mask 7 and the tooth bar 6) and also to obtain a maximum filling factor and optimum SNR.

This example assembly is for neuroimaging of an anesthetized, in the case of this particular example, for a mouse. The animal is held in position by the use of three mechanisms that are very quickly implemented and minimise the set-up time and so reduce the stress for the animal. This assembly also allows for a relaxed work-flow without the need for time consuming stereotactic positioning of the animal.

Figures 1, 2:
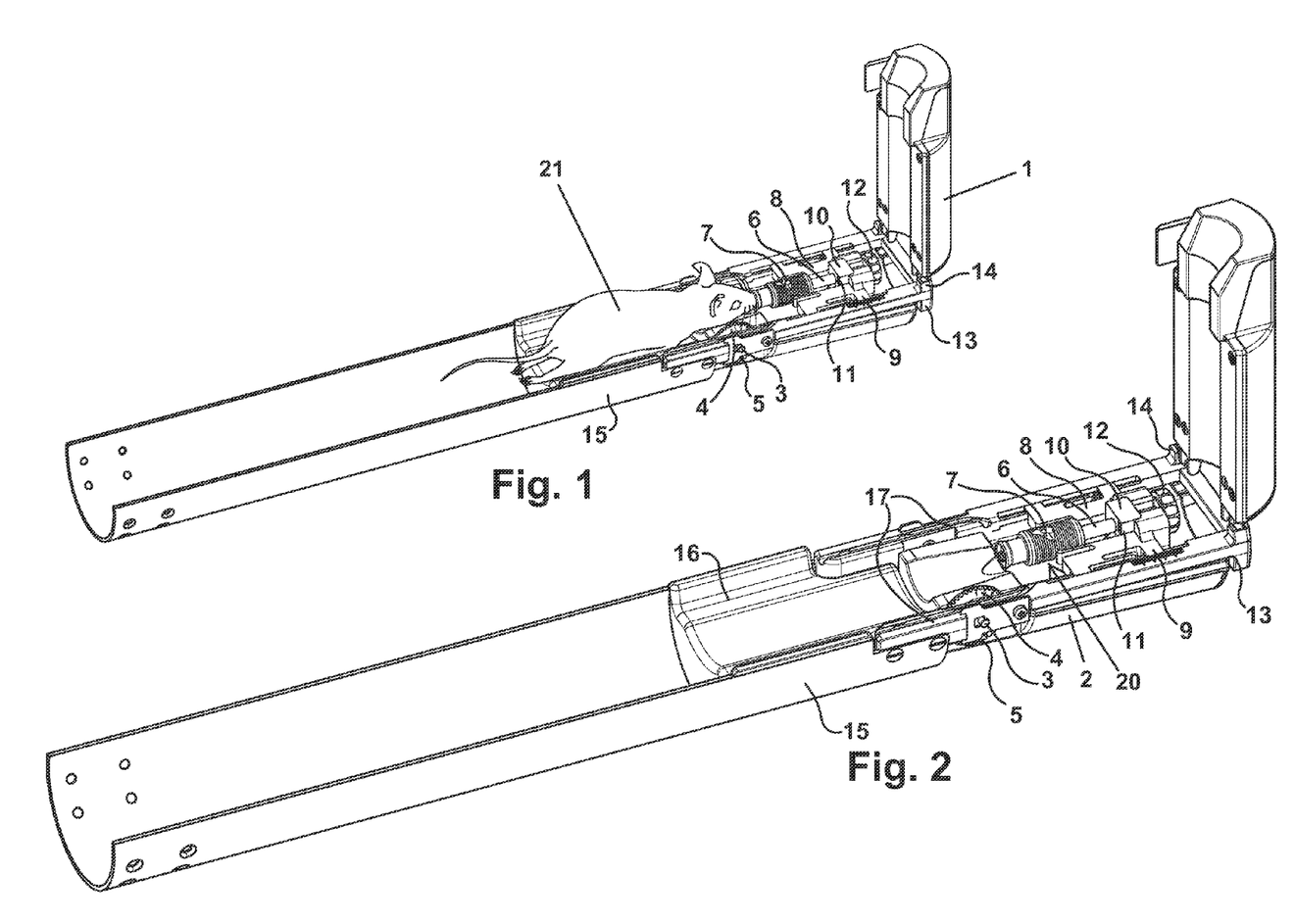
FIG. 1 is a perspective view of an example restraining assembly with rodent.
FIG. 2 is a perspective view of the example restraining assembly of FIG. 1 without rodent.
Figure 5:
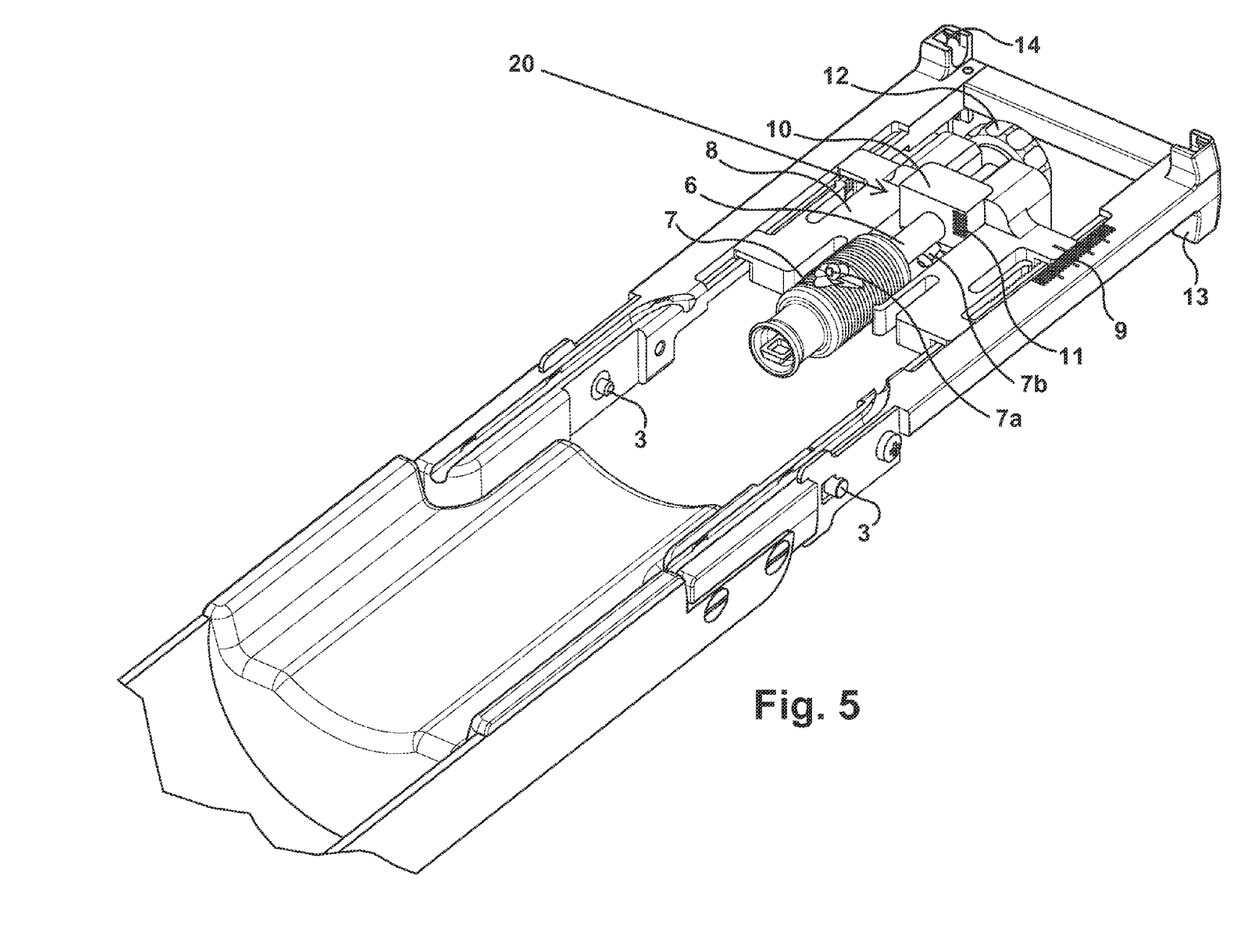
FIG. 5 is a perspective view of the close-up of the part of the example restraining assembly of FIG. 3 showing details of the middle part.

With the new workflow, as shown in FIG. 1, the teeth of the animal are placed inside the catch of the tooth bar 6. Then, the anaesthetic gas mask 7 is slid over the snout of the animal 21. The shape of the gas mask 7 is ergonomically adapted to the specific animal, and clamps the sides of the snout so that the animal head is locked. The animal rests on the animal couch 16 (FIG. 2). As shown in FIG. 5, the gas mask 7 feeds an anaesthetic agent via the gas inlet 7a to the animal. The used gas is let out on the gas outlet 7b.

Figure 8:
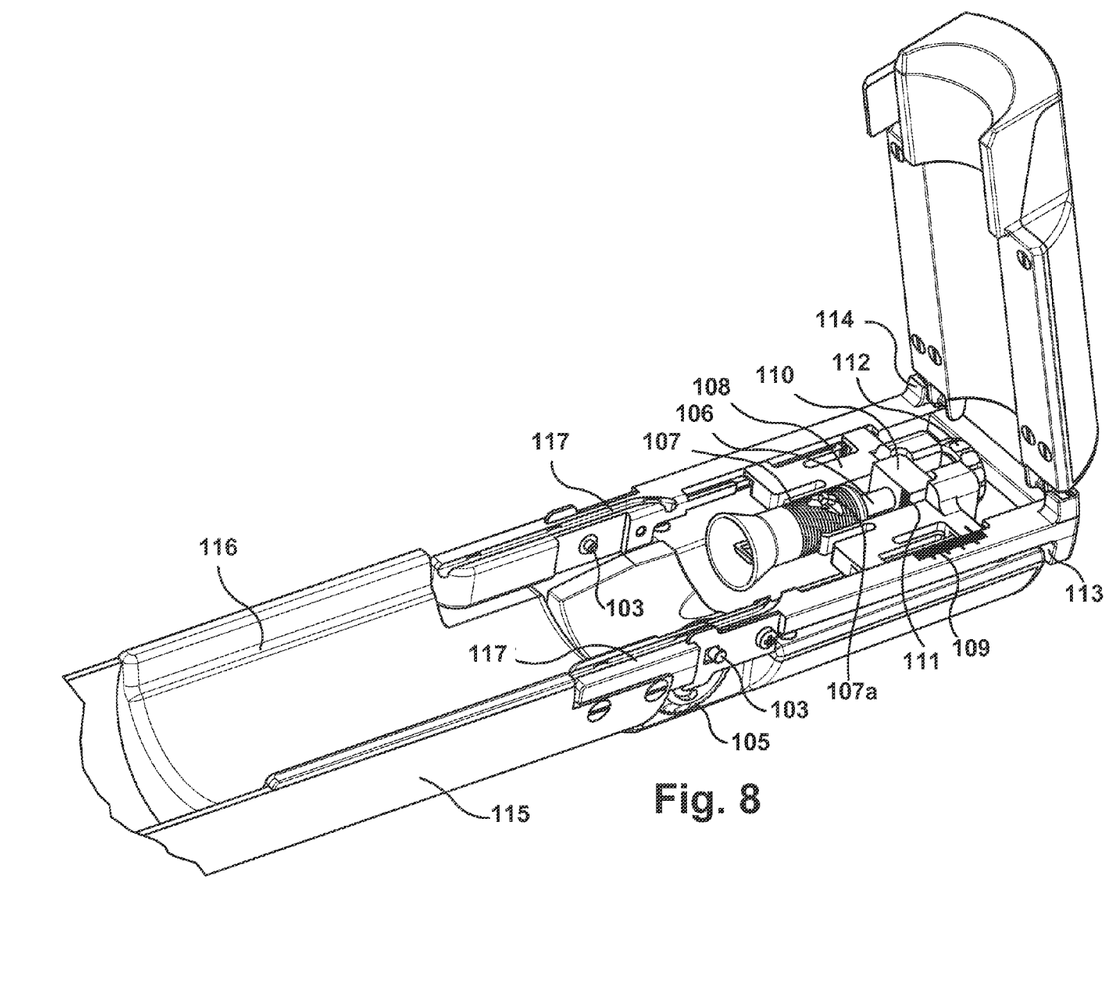
FIG. 8 shows a perspective view of another example embodiment of the restraining assembly with top part pivoted open.
Figure 9:
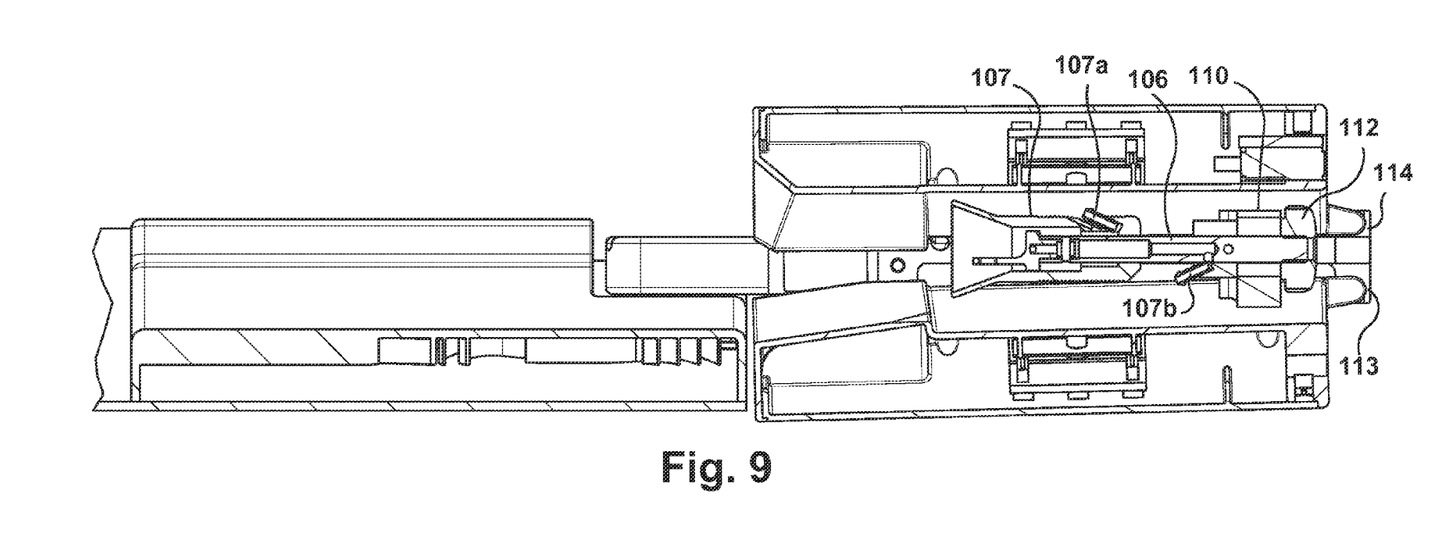
FIG. 9 is a semi-sectional view from an orthogonal direction towards the sagittal plane of the example restraining assembly of FIG. 8 with the top and bottom parts put in the operating position.

Alternatively, the animal can be anaesthetized utilizing the anaesthetic unit 20 that has been previously removed from the assembly. Then, the animal with the anaesthetic unit 20 is placed in the assembly where the anaesthetic unit 20 is simply clipped into the coil holder 17 and properly positioned. This allows interventional applications and, for example, intubation of the animal. The straightforward installation of the anaesthetic block also allows it to be easily exchanged for another sized unit (e.g. exchange between rat and mouse). Rat adaptations are shown in FIGS. 8-9.

Figure 3:
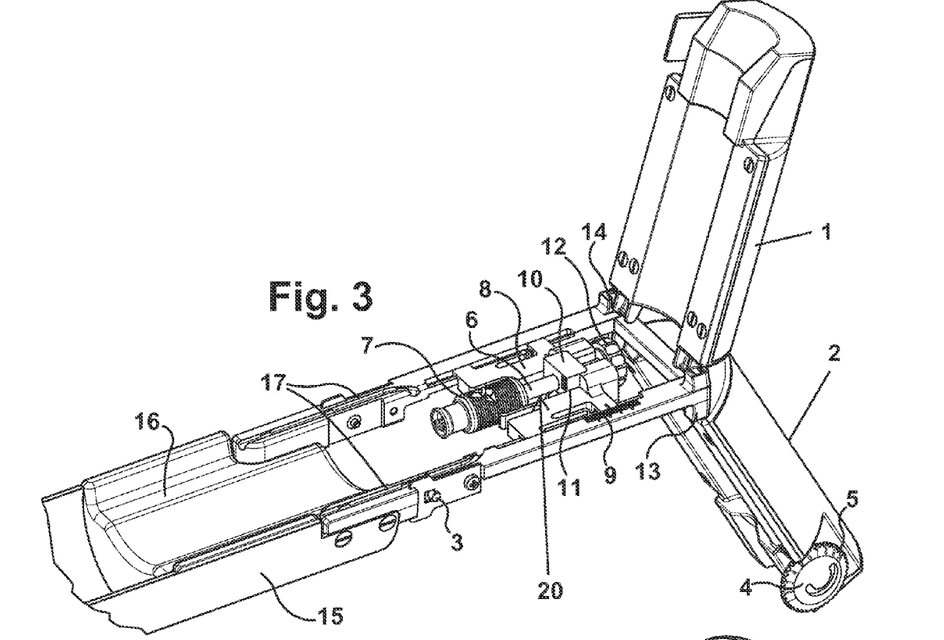
FIG. 3 is a perspective view of a close-up of a part of the example restraining assembly of FIG. 2 showing a bottom part and a top part pivoted open.
Figure 4:
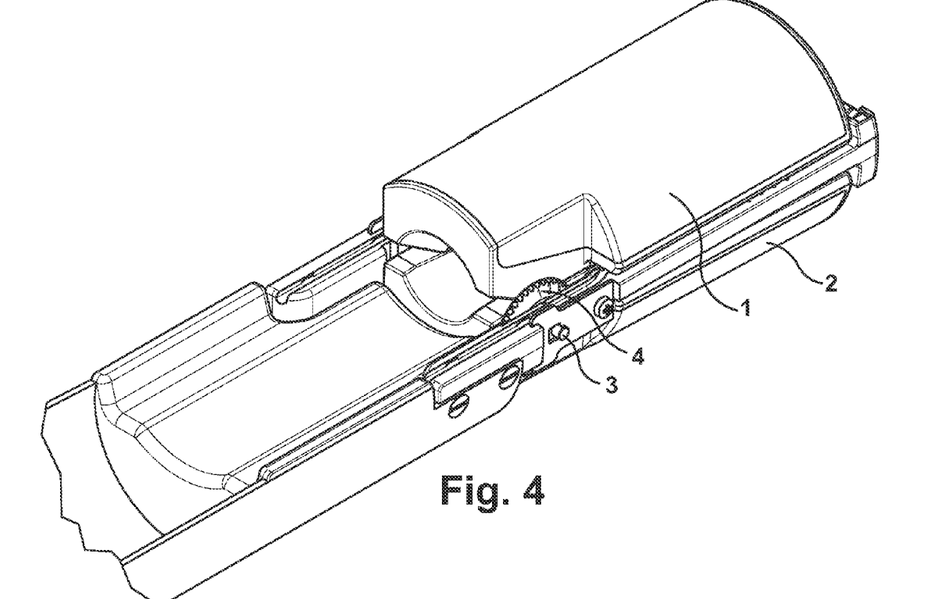
FIG. 4 is a perspective view of the close-up of the part of the example restraining assembly shown in FIG. 3 with the bottom part and the top part closed in an operating position.

As shown in FIG. 5, the position of both the tooth bar 6 and the gas mask 7 can be freely adjusted with the horizontally sliding anaesthetic holder 8, and the vertical sliding anaesthetic block 10. As shown in FIGS. 1-3, each of those mechanisms incorporates scales 9, 11 to allow reproducible positioning.

The animal head should be positioned so that the skull is placed directly against the bottom of the top part 1 of the array coil. This position can be further secured by adjusting the height of the bottom part 2 of the array coil. Its inner shape is anatomically formed so that the head of the animal is well supported. The height of the bottom part 2 of the array coil is adjusted depending on the size of the animal head. This is done easily with the adjustment wheel 4, which has a scale 5 to allow for reproducibility (see FIG. 3). After this adjustment, the final position of the tooth bar and the gas mask is locked by tightening the locking wheel 12.

This set-up allows for a large range of adjustments. The described work-flow positions the head of the animal securely with little effort, and in very little time compared to the previously described state-of-the-art procedure. This minimizes stress to the animal, and reduces the set up time. It also increases the throughput for a more efficient use of the equipment. The adjustable positioning allows a flexible set up of the assembly while the scaling ensures reproducible positioning.

Both the top part 1 and the bottom part 2 of the head coil can include a pre-amplifier (not shown) for amplifying the signal obtained by the respective part. Such an amplifier can be provided within the housing of each of the parts, or provided outside of the housing, as desired.

Both, the top part 1 and the bottom part 2 of the head coil can be hinged away from the assembly to give access to the animal, as shown in FIG. 3. The pivots 13, 14 is located in the coil holder 17 of the array coil. The coil holder 17 can be attached to the semi-tube 15, which holds the animal bed 16. Using the wings, the locking pins 3 can be pulled outwards and each array coil part 1, 2 can be hinged away giving free access to the anaesthetic unit 20 (and the positioned animal 21). To lock the coil parts 1, 2 again in the adjusted position, they are clipped back again and will lock automatically when the pin 3 is latched.

The top part 1 of the array coil locks when the pin 3 falls in a hole placed in a hook on the side of the assembly. The adjustable bottom part 2 of the coil is locked when the pin 3 falls in a spiral shaped notch in the adjustment wheel 4. This spiral shaped notch allows the adjustment of the height of the bottom part of the coil. By turning the adjustment wheel 4, the horizontal position of the notch (and the locked pin) changes. A friction plate is provided that also acts as a hub for the adjustment wheel 4 that increases the force needed to turn the wheel, and so avoids unwanted changes of the bottom coil part position.

Figure 6:
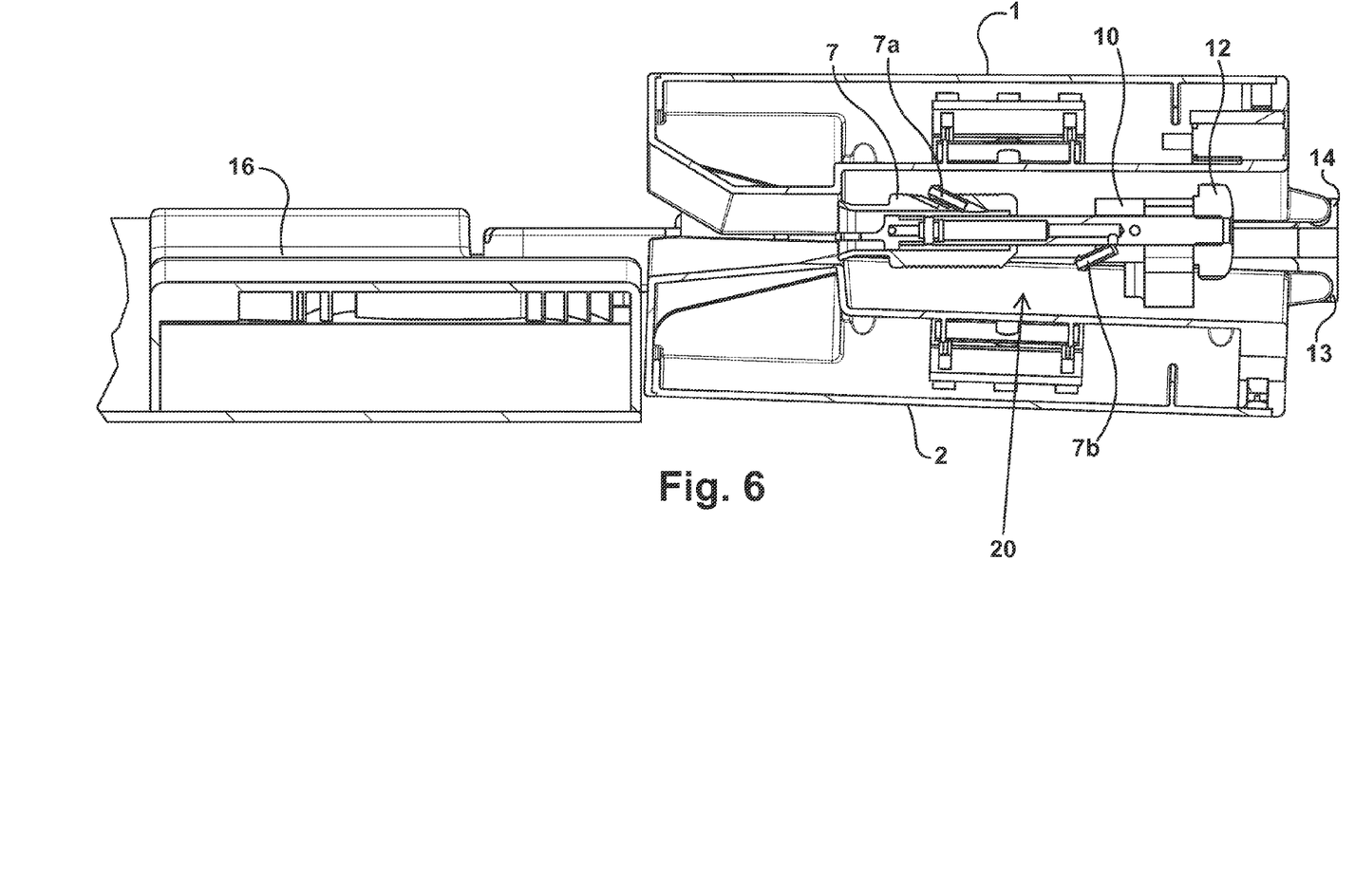
FIG. 6 is a semi-sectional view from an orthogonal direction towards the sagittal plane of the part of FIG. 5 with the bottom and top parts put in the operating position.

FIG. 6 shows a view of a cut through the sagittal plane of the mouse assembly in operating position. The semi-tube 15 is not shown completely here. The top coil half 1 is locked in position whereas the bottom coil half 2 is adjusted into its highest position to fit comparatively small sized mouse heads.

The animal is to be laid on top of the animal bed 16 with its snout fixed in position by the anaesthetic gas mask 7. Here the anaesthesia is applied to the animal through the gas inlet 7a and the gas outlet 7b.

The position of the anaesthetic gas mask 7 is adjusted through the anaesthetic block 10 and fixed in position with the locking wheel 12.

Figure 7:
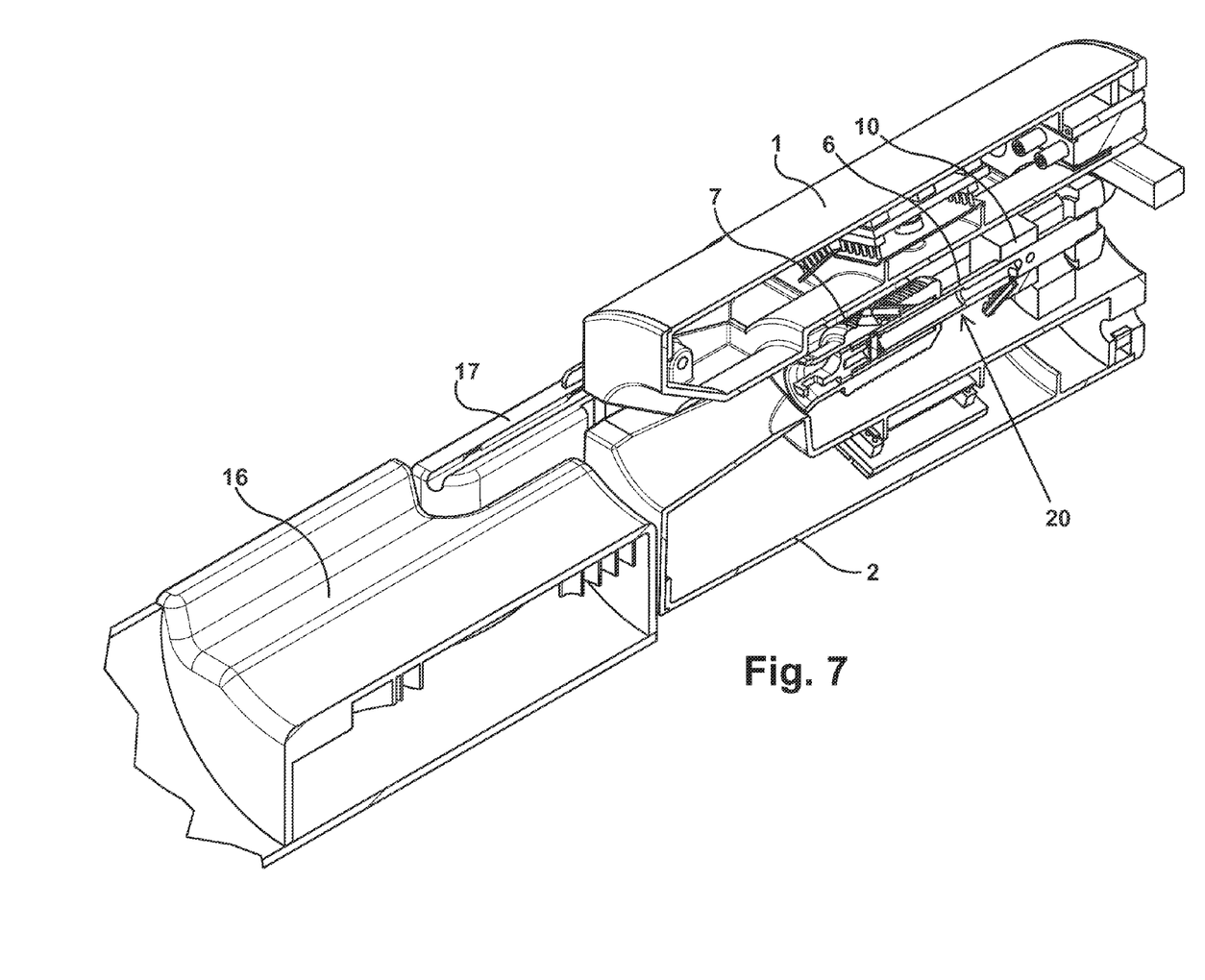
FIG. 7 is a perspective view of the semi-sectional view of FIG. 6.

FIG. 7 shows the same assembly from an oblique angle. In addition to FIG. 6, it shows how the anaesthetic gas mask 7 is attached to the anaesthetic block 10 by the tooth bar 6. It also shows the attachment of the coil assembly to the animal couch 16 by the coil holder 17.

FIGS. 8 and 9 show another example embodiment of the assembly device adapted for use with a larger rodent such as a rat. This device has a top part 101 of the array coil; a bottom part 102 of the array coil; a locking pin 103 including wings to pull outwards; an adjustment wheel 104 for positioning the bottom part of the array coil; a scale 105 on the adjustment wheel 104 for reproducible positioning; a tooth bar 106 to fixate the skull of the animal; an anaesthetic gas mask 107 having a gas inlet 107a and a gas outlet 107b; an anaesthetic holder 108, a scale 109 for horizontal positioning of the anaesthetic holder; an anaesthetic block 110 for vertical adjustment with a scale 111 for vertical adjustment of the anaesthetic block, and a locking wheel 112 to fix the positioning; a pivot 113 for bottom part of the array coil; a pivot 114 for top part of the array coil; a semi tube 115 to hold the assembly; an animal couch 116; and a coil holder 117. These components operate similarly to the corresponding components discussed above for the first example embodiment for a mouse-sized rodent, except that the components are scaled larger to accommodate the larger body of a rat.

For neuroimaging using either of the above embodiments, it is desirable to have a good Signal to Noise Ratio (SNR) so it is desirable to use surface coils. Here, coil arrays have developed rapidly over the last few years. However there are practical limitations with the use of array coils as the available space is limited so that only a small number of array elements can be implemented around a small animal head.

By the use of a split (top and bottom) array, we use the excellent SNR of surface coils and combine it with the good homogeneity of volume coils. The sensitivity profiles of the top and bottom coil parts superimpose and produce much more homogeneous signal intensity. The coil adjustment allows a positioning of the array parts according to the actual size of the animal and, thus, optimizes the filling factor of the coil. For the investigation of sub-surface structures within the animal head, an additional coil spacing of only a few millimeters can reduce the filling factor dramatically, and can easily result in an SNR drop of 20% or more. A good homogeneity is very important for qualitative measurements and QA set-ups. Here, a small positioning error can lead to large changes in the signal intensity and affect the measurement.

With the use of the two coil parts 1, 2, twice the number of coil elements can be implemented allowing one to maximise the overall SNR (a 40% increase has been observed in the centre of an animal head), and increase the signal homogeneity. For MR neuro-imaging applications, mostly the animal brain is investigated. In this case, the top part of the array will produce the most NMR signal due to its proximity. However, the bottom part of the array will still distribute signal to the lower part of the brain, and keep the signal intensity much more constant over the imaging volume that with only surface coil positioned on top of the skull.

With the symmetrically split array coil arrangement, it is also possible to easily implement quadrature MR transmit coils. In this case, the transmit field is composed of two orthogonal components of similar amplitude, but with a 90° phase shift. The corresponding coils can be easily accommodated in the split coil design.

Quadrature coils can be utilized in order to gain SNR. For this, two geometrically orthogonal coil elements are combined via a quadrature hybrid, including a 90° phase shift. The typical gain of SNR by quadrature coils is up to a factor of 1.4. This technique can be applied to the disclosed embodiments doing either a single quadrature channel and leaving the others in linear operation, or doing even more than one channel in quadrature operation. The choice of number of channels might depend upon the geometry and size of the coil elements, the orientation in the static magnetic BO field, or the loading condition of the object under investigation. See Haase et al. "NMR probeheads for in-vivo applications; Concepts of Magnetic Resonance" pp 361 (2000) incorporated herein by reference.

The described assembly is designed so that the animal is positioned with the body placed on top of an animal bed. This bed can be used as a heating mat to control the animal's body temperature and keep it constant. The temperature is adjusted by the means of heated air that flows through one or more part of the assembly. This heated air can also flow completely or only partially inside the volume transmit coil in which the herein described assembly is usually placed for MR investigations.

Similar arguments as with the head array apply for MR investigations of the animal's heart. In this case, a split coil design is used with a bottom part where the animal lies on and a top part that is positioned once the animal is brought into the correct position. Here, some small spacing between the animal and the top part of the heart should be allowed for as there will be some breathing motion. Alternatively, a flexible coil design can be used to adapt the coil shape to the imaged animal and allow for cardiac and respiratory motion. This is particularly useful when animals of different sizes are examined. The weight of rats, for example, can vary by a factor of 5, so that it is important to be able to adapt the coil shape, size and position to the imaged animal. Such set-up with a bottom part and a top part of the heart array, with the option of a flexible coil housing, provides an increased filling factor and enhances the image SNR.

The heart array is anatomically shaped and positioned instead of the animal bed. The heart array can also be used to control the animal's temperature with the means of heated air that flows through the structure. Both, the head coil and the heart coil can be positioned and operated independent from one another. Here the operator can freely decide throughout the experiment which investigation (head or brain) should be performed next.

The invention has been described hereinabove using specific examples and example embodiments; however, it will be understood by those skilled in the art that various alternatives may be used and equivalents may be substituted for elements and/or steps described herein, without deviating from the scope of the invention. Modifications may be necessary to adapt the invention to a particular situation or to particular needs without departing from the scope of the invention. It is intended that the invention not be limited to the particular implementations and embodiments described herein, but that the claims be given their broadest interpretation to cover all embodiments, literal or equivalent, disclosed or not, covered thereby.

What is claimed is:

1. An apparatus for supporting the imaging of an animal, comprising:
    an animal bed;
    a first part positioned with said bed for supporting a part of the animal and receiving a first imaging signal from a first portion of the animal;
    a second part connected to said bed for receiving a second imaging signal from a second portion of the animal; and
    an adjustment mechanism for adjusting a height of the first part to accommodate the size of the head of the animal, said adjustment mechanism comprising:
        an adjusting wheel,
        a horizontally sliding anesthetic holder, and
        a vertically adjustable anesthetic block, wherein
        a height of the first part can be adjusted with the adjusting wheel and where the adjusted position can be locked;
    wherein
    said first part and said second part are separately moveable with respect to said animal bed, and wherein
    at least one of said first part and/or said second part are adjustable to independently configure the apparatus for a size of a particular animal for improving receiving the first imaging signal and/or the second imaging signal.

2. The apparatus of claim 1, wherein said first part is adjustable in height with respect to said bed and wherein said second part includes a removable connection for connecting to said bed for allowing removal of said second part from said bed.

3. The apparatus of claim 1, wherein said first portion of the animal is an upper portion of the animal including the head and/or torso of the animal and wherein said second portion of the animal is a lower portion of the animal.

4. The apparatus of claim 1, wherein said mechanism is adapted such that an adjustment of said mechanism is reproducible when the animal is removed from and then replaced in said apparatus.

5. The apparatus of claim 4, wherein said mechanism includes a scale for indicating a height position.

6. The apparatus of claim 1, wherein an inner portion of said second part is anatomically formed to accommodate the head of the animal.

7. The apparatus of claim 1, wherein said part of the animal supported by said first part is at least a part of the head of the animal.

8. The apparatus of claim 1, wherein said first part can be pivoted away from said animal bed in one direction, and wherein said second part can be pivoted away from said animal bed in another direction.

9. The apparatus of claim 1, wherein said first part can be removed from said bed and wherein said apparatus is thereby adapted for use in imaging the animal using said first part without said second part.

10. The apparatus of claim 1, wherein an inner portion of said second part is anatomically formed to accommodate the head of the animal.

11. An apparatus for supporting the imaging of an animal, comprising:
    an animal bed;
    a first part positioned with said bed for supporting a part of the animal and receiving a first imaging signal from a first portion of the animal;
    a second part connected to said bed for receiving a second imaging signal from a second portion of the animal;

an adjustment mechanism for adjusting a height of the first part to accommodate the size of the head of the animal, said adjustment mechanism comprising:
an adjusting wheel,
a horizontally sliding anesthetic holder, and
a vertically adjustable anesthetic block, wherein
a height of the first part can be adjusted with the adjusting wheel and where the adjusted position can be locked;
ear pins for positioning the animal that is anaesthetized; and
a tooth bar in combination with a gas mask for clamping the snout of the animal, wherein
said first part and said second part of said apparatus are adapted to be ergonomically shaped to fix the head of the animal in a desired position, and wherein
said first part and said second part are separately moveable with respect to said animal bed, and further wherein
at least one of said first part and/or said second part are adjustable to independently configure the apparatus for a size of a particular animal for improving receiving the first imaging signal and/or the second imaging signal.

12. An apparatus for supporting the imaging of an animal, comprising:
an animal bed;
a bottom array part connected to said bed and including a first coil adapted for receiving a first imaging signal from a lower part of the animal,
a top array part including:
a second coil adapted for receiving a second imaging signal from the head and/or torso of the animal, and
a removable connection connected to said bed for allowing said top part to be removed from said bed and also for allowing said top part to be pivoted away from said second part;
an adjustment mechanism for adjusting a height of said bottom array part to accommodate the size of the head of the animal in a repeatable manner;
an anesthetic unit connected to said bed and provided within said bottom array part and said top array part when closed, wherein when said top array part is pivoted away from said bottom array part, access is provided to said anesthetic unit; and
a head holding mechanism connected to said bed for holding the head of the animal in a fixed position.

13. The apparatus of claim 12, wherein both said bottom array part and said top array part can be pivoted away from each other to permit internal access.

14. The apparatus of claim 12, wherein said top array part includes an inner portion that is anatomically formed to accommodate the head and/or torso of the animal.

15. The apparatus of claim 12, wherein said bottom array part is adapted to be pivoted away from said top array part to provide access to said anesthetic unit.

16. The apparatus of claim 15, wherein said bottom array part is adapted to be locked in place for imaging the animal.

17. The apparatus of claim 12, wherein said top array part is adapted to be locked in place for imaging the animal.

18. The apparatus of claim 12, further comprising a friction plate interacting with said adjustment mechanism to prevent inadvertent misadjustment.

19. An apparatus for supporting the imaging of an animal, comprising:
an animal bed;
a bottom array part including:
a bottom part connection mechanism for connecting to said bed in a pivoting manner;
a bottom part locking mechanism for locking the bottom part in place for imaging the animal, and
a first coil adapted for receiving a first imaging signal from a lower part of the animal;
a top array part including:
a top part connection mechanism for connecting to said bed in a pivoting and removable manner,
a top part locking mechanism for locking said top part in place for imaging the animal,
a second coil adapted for receiving a second imaging signal from the head and/or torso of the animal, and
an inner portion that is anatomically formed to accommodate the head and/or torso of the animal;
an adjustment mechanism for adjusting a height of said bottom array part to accommodate the size of the animal in a repeatable manner;
a friction plate interacting with said adjustment mechanism to prevent inadvertent misadjustment;
an adjustment locking mechanism for locking the adjustment mechanism in place for imaging the animal;
a removable anesthetic unit connected to said bed and provided within said bottom array part and said top array part, wherein when said top array part is pivoted away from said bottom array part, access is provided to said anesthetic unit, wherein
access to said anesthetic unit and/or the animal is provided by pivoting said top array part and said bottom array part away from each other.

20. The apparatus of claim 19, further comprising a heart coil array to allow for the option of the animal head or its heart being investigated.

21. The apparatus of claim 19 wherein a heart coil is used for imaging the animal's heart, wherein the heart coil is comprised of a single sided surface design (anterior) or of an anterior and a posterior part in a sandwich setup, and wherein both the top array part and the bottom array part can either be rigid or flexible such that a flexible part allows for optimization of different animal sizes, wherein the top array part, the bottom array part, and the heart coil are used as one entity even if only heart- or only brain investigations are being performed.

22. An apparatus for supporting the imaging of an animal, comprising:
an animal bed;
a first part positioned with said bed for supporting a part of the animal and receiving a first imaging signal from a first portion of the animal;
a second part connected to said bed for receiving a second imaging signal from a second portion of the animal; and
an adjustment mechanism for adjusting a height of the first part to accommodate the size of the head of the animal, said adjusting mechanism including: an adjusting wheel, a horizontally sliding anesthetic holder, and a vertically adjustable anesthetic block, wherein a height of the first part can be adjusted with the adjusting wheel and where the adjusted position can be locked.

* * * * *